(12) United States Patent
Purohit et al.

(10) Patent No.: US 9,145,406 B2
(45) Date of Patent: Sep. 29, 2015

(54) PROCESS FOR PREPARING DASATINIB MONOHYDRATE

(71) Applicant: SHILPA MEDICARE LIMITED, Raichur (IN)

(72) Inventors: Prashant Purohit, Vizianagaram (IN); Sriram Rampalli, Vizianagaram (IN); Mohanrao Seshagiri Vijaya Murali, Vizianagaram (IN); Lavkumar Upalla, Vizianagaram (IN); Pradeep Pothana, Vizianagaram (IN)

(73) Assignee: SHILPA MEDICARE LIMITED, Rajendra Gunj, Raichur Karnataka (IN)

( * ) Notice: Subject to any disclaimer, the term of this patent is extended or adjusted under 35 U.S.C. 154(b) by 0 days.

(21) Appl. No.: 14/382,557

(22) PCT Filed: Apr. 16, 2013

(86) PCT No.: PCT/IN2013/000253
§ 371 (c)(1),
(2) Date: Sep. 3, 2014

(87) PCT Pub. No.: WO2013/157019
PCT Pub. Date: Oct. 24, 2013

(65) Prior Publication Data
US 2015/0057446 A1  Feb. 26, 2015

(30) Foreign Application Priority Data
Apr. 20, 2012 (IN) .......................... 1576/CHE/2012
Jul. 5, 2012 (IN) .......................... 2715/CHE/2012

(51) Int. Cl.
C07D 417/12  (2006.01)

(52) U.S. Cl.
CPC .................................. C07D 417/12 (2013.01)

(58) Field of Classification Search
CPC .................................................... C07D 417/12
See application file for complete search history.

(56) References Cited

U.S. PATENT DOCUMENTS

| 6,235,936 | B1 * | 5/2001 | Buchwald et al. | ............ | 564/386 |
| 6,596,746 | B1 | 7/2003 | Das et al. | | |
| 7,491,725 | B2 * | 2/2009 | Lajeunesse et al. | ..... | 514/252.19 |
| 2002/0022575 | A1 * | 2/2002 | Fischer et al. | ................ | 504/221 |

FOREIGN PATENT DOCUMENTS

| CN | 102010407 A | 4/2011 |
| WO | 2007106879 A2 | 9/2007 |
| WO | 2010139979 A2 | 12/2010 |
| WO | 2010139980 A1 | 12/2010 |
| WO | 2010139981 A2 | 12/2010 |

* cited by examiner

Primary Examiner — Valerie Rodriguez-Garcia

(57) ABSTRACT

The present invention relates to an improved process for preparation of Dasatinib monohydrate Formula A,

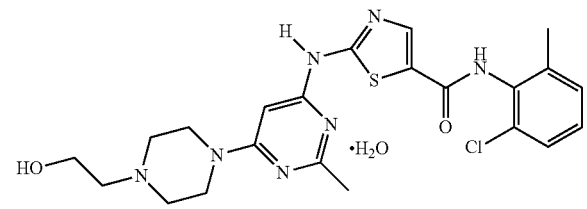

comprising the steps of:
a) reacting the compound of Formula I with 1-(2-Hydroxyethyl)piperazine (Formula II) in the presence of acetonitrile solvent, an organic base and a phase transfer catalyst;

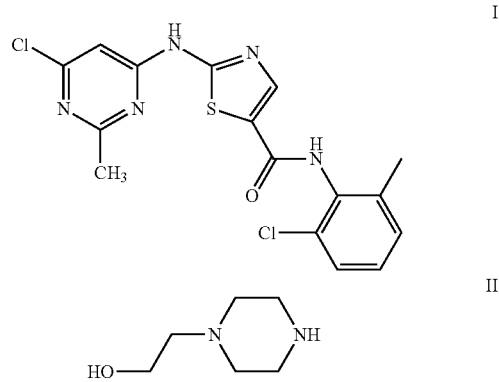

b) heating the reaction mixture at 50-80° C.;
c) adding water to the reaction mass obtained in step b);
d) cooling the reaction mixture to a temperature below 35° C.;
e) filtering and drying the material obtained in step d);
f) optionally purifying the product obtained from step e);
g) isolating the crystalline Dasatinib monohydrate.

11 Claims, 2 Drawing Sheets

PROCESS FOR PREPARING DASATINIB MONOHYDRATE

FIELD OF INVENTION

The present invention provides an improved process for preparing N-(2-chloro-6-methylphenyl)-2-[[6-[4-(2-hydroxyethyl)-1-piperazinyl]-2-methyl-4-pyrimidinyl]amino]-5-thiazole carboxamide monohydrate or Dasatinib monohydrate (Formula A).

Formula A

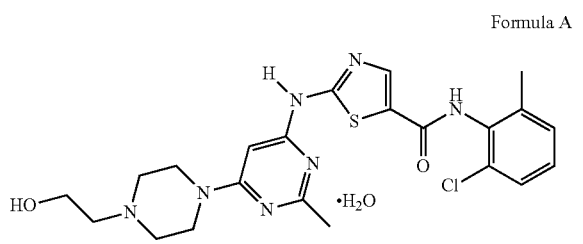

BACKGROUND OF THE INVENTION

Dasatinib is a cyclic protein tyrosine kinase inhibitor indicated for newly diagnosed adults with Philadelphia chromosome-positive (Ph+) chronic myeloid leukemia (CML) in chronic phase; adults with chronic, accelerated, or myeloid or lymphoid blast phase Ph+ CML with resistance or intolerance to prior therapy including imatinib; and, adults with Philadelphia chromosome-positive acute lymphoblastic leukemia (Ph+ ALL) with resistance or intolerance to prior therapy. It is also being evaluated for use in numerous other cancers, including advanced prostate cancer.

Dasatinib is chemically described as N-(2-chloro-6-methylphenyl)-2-[[6-[4-(2-hydroxyethyl)-1-piperazinyl]-2-methyl-4-pyrimidinyl]amino]-5-thiazole carboxamide. It is approved in USFDA as SPRYCEL™ and is chemically mentioned in the label as N-(2-chloro-6-methylphenyl)-2-[[6-[4-(2-hydroxyethyl)-1-piperazinyl]-2-methyl-4-pyrimidinyl]amino]-5-thiazolecarboxamide, monohydrate.

Formula A

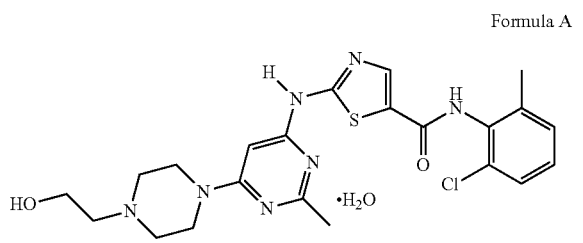

It is a white to off-white powder, insoluble in water and slightly soluble in alcoholic solvents like ethanol and methanol.

Das et al, in U.S. Pat. No. 6,596,746 B1 provided the first disclosure of N-(2-chloro-6-methylphenyl)-2-[[6-[4-(2-hydroxyethyl)-1-piperazinyl]-2-methyl-4-pyrimidinyl]amino]-5-thiazole carboxamide or Dasatinib, which also describes the process for preparing Dasatinib.

Further to this Lajeunesse et al. in U.S. Pat. No. 7,491,725 B2 provided the crystalline monohydrate, crystalline butanol solvate, crystalline ethanol solvate and neat forms of Dasatinib. U.S. Pat. No. 7,491,725 B2 also provides processes for the preparation of these mentioned forms of Dasatinib. Scheme I shows one of the process for the preparation of Dasatinib according to U.S. Pat. No. 7,491,725 B2.

Scheme I

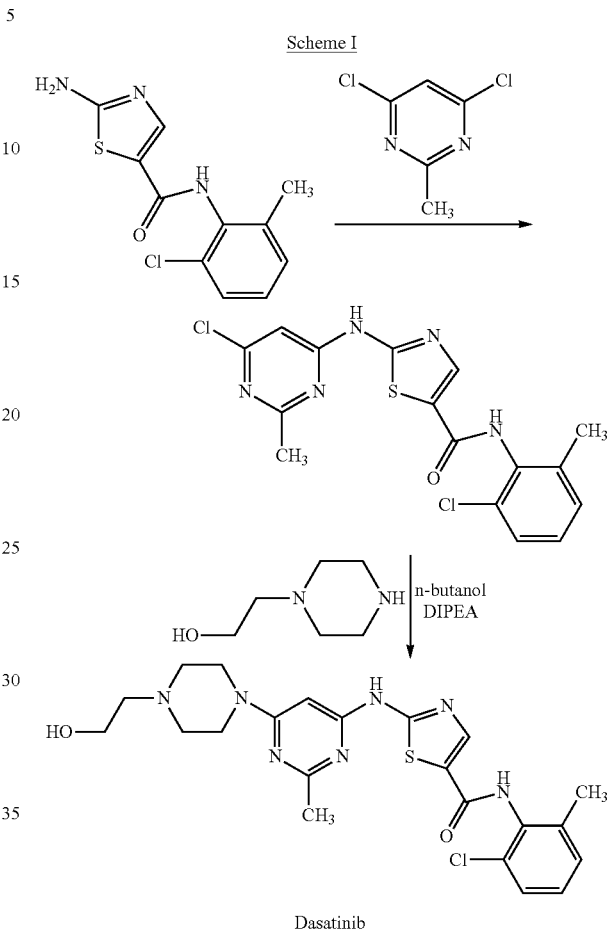

Dasatinib

It has been mentioned in this patent that Dasatinib can be further converted into its monohydrate by methods such as heating the Dasatinib free base solution in aqueous ethanol solution; or by seeding aqueous acetate salt of Dasatinib or aqueous suspension of Dasatinib with its monohydrate form and heating; or treating a solution of Dasatinib in solvents such as NMP or DMA with water. However, the yield % of the mentioned processes is quite low (~80%), to be economical for industrial set-up.

Further review of the available literature regarding Dasatinib monohydrate discloses various other processes for its preparation but due to one or more drawbacks with respect to the production of side products, the use of expensive coupling reagents, less than desirable yields, and the need for multiple reaction steps, most of them are not particularly convenient and economical for industrial scale-up.

Hence, there is an unmet need to develop improved, cost-effective and industrially amenable processes for the preparation of Dasatinib monohydrate involving less number of steps and providing higher yield of end product with better purity.

Therefore, inventors of the present application provide a simple high yielding process for preparation of highly pure Dasatinib monohydrate, which overcomes the disadvantages associated with prior disclosed literature methods.

SUMMARY OF THE INVENTION

Particular aspects of the present specification relate to the improved process for preparation of N-(2-chloro-6-methylphenyl)-2-[[6-[4-(2-hydroxyethyl)-1-piperazinyl]-2-methyl-4-pyrimidinyl]amino]-5-thiazole carboxamide monohydrate or Dasatinib monohydrate (Formula A).

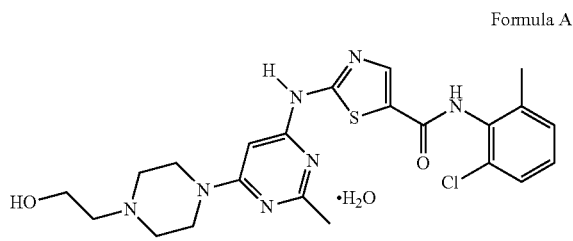

Formula A

In one aspect of the present application, the present invention provides process for preparing crystalline Dasatinib monohydrate characterized by X-ray powder diffraction pattern as per FIG. 1 and DSC pattern as per FIG. 2.

In another aspect of the present application, it relates to the process for preparing Dasatinib monohydrate of Formula A comprising the steps of— a) reacting the compound of Formula I with 1-(2-Hydroxyethyl)piperazine (Formula II) in the presence of acetonitrile solvent, an organic base and a phase transfer catalyst;

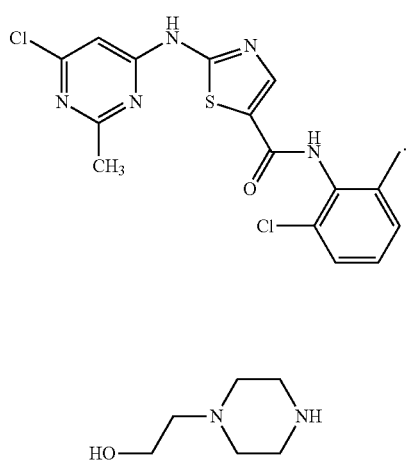

b) heating the reaction mixture at 70-80° C.;
c) adding water to the reaction mass obtained in step b);
d) cooling the reaction mixture to a temperature below 35° C.;
e) filtering and drying the material obtained in step d);
f) Optionally purifying the product obtained from step e);
g) isolating the crystalline Dasatinib monohydrate.

In a further aspect of the present application, it relates to the process for preparing compound of Formula I

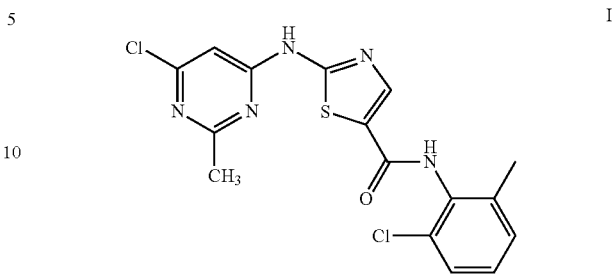

which is a key starting material for the preparation of Dasatinib monohydrate, by reaction of 2-amino-N-(2-chloro-6-methyl phenyl)-5-thiazole carboxamide with 4,6-dichloro-2-methyl pyrimidine in the presence of sodium amide ($NaNH_2$).

In still another aspect of the present application, Dasatinib monohydrate prepared according to the process of the present invention has the moisture content ranging between 3.4 to 4.2%.

Further particular aspects of the invention are detailed in the description of invention, wherever appropriate.

DETAILED DESCRIPTION

Figure 1:
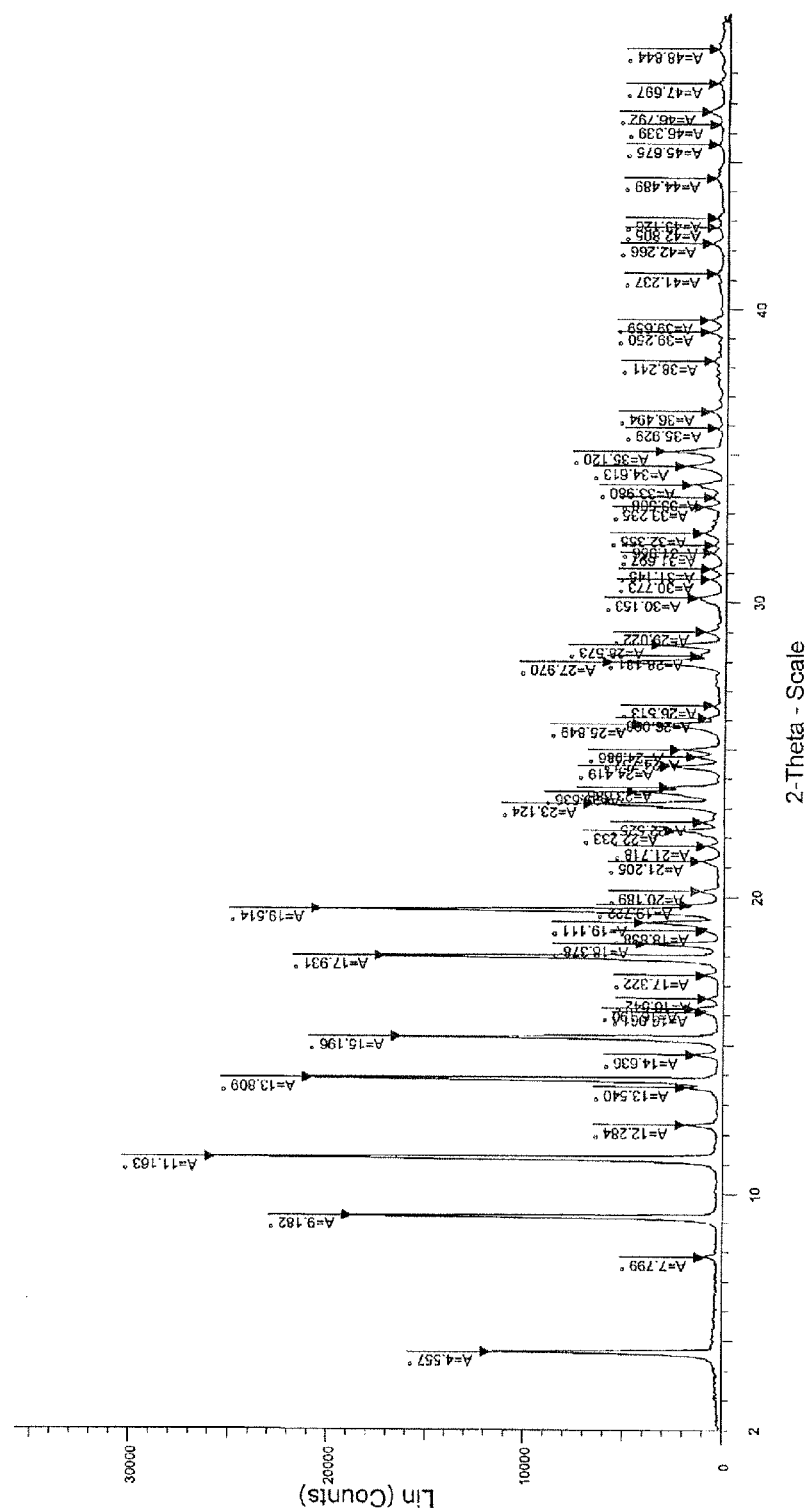
FIG. 1 is PXRD of Dasatinib monohydrate obtained according the process of example 1.

As set forth herein, embodiments of the present invention relate to an improved process for preparation of N-(2-chloro-6-methylphenyl)-2-[[6-[4-(2-hydroxyethyl)-1-piperazinyl]-2-methyl-4-pyrimidinyl]amino]-5-thiazole carboxamide monohydrate or Dasatinib monohydrate (Formula A).

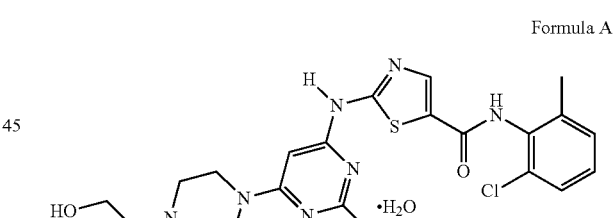

Formula A

In an embodiment of the present application, it provides a process for preparation of Dasatinib monohydrate, comprising the steps of— a) reacting the compound of Formula I with 1-(2-Hydroxyethyl)piperazine (Formula II) in the presence of acetonitrile solvent, an organic base and a phase transfer catalyst;
b) heating the reaction mixture at 70-80° C.;
c) adding water to the reaction mass obtained in step b);
d) cooling the reaction mixture to a temperature below 35° C.;
e) filtering and drying the material obtained in step d);
f) optionally purifying the product obtained from step e);
g) isolating the crystalline Dasatinib monohydrate.

The individual steps of the process according to the present invention for preparing Dasatinib monohydrate are detailed separately herein below:

Step a) comprises reacting the compound of Formula I with 1-(2-Hydroxyethyl)piperazine (Formula II) in the presence of solvent acetonitrile, an organic base and a phase transfer catalyst;

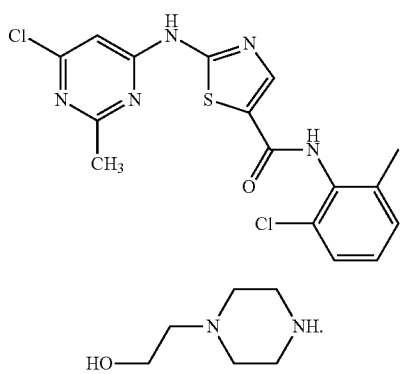

2-((6-chloro-2-methylpyrimidin-4-yl)amino)-N-(2-chloro-6-methylphenyl)thiazole-5-carboxamide of Formula I is reacted with 1-(2-Hydroxyethyl)piperazine of Formula II in the presence of organic base selected from triethyl amine (TEA), diisopropylethyl amine (DIPEA), t-butylamine or propyl amine and a phase transfer catalyst selected from tetrabutyl ammonium bromide (TBAB), tetrabutyl ammonium fluoride (TBAF) or benzyl triethyl ammonium chloride.

The compound of Formula I, used in this reaction may be obtained from any source/method described in the prior art or from the process described later here in this specification.

The amount of 1-(2-Hydroxyethyl)piperazine of Formula II used for this reaction ranges from 4-8 equivalents (in moles) as compared to the amount in moles of compound of Formula I. Amount of acetonitrile solvent utilized for this reaction may vary from 10 to 25 times (vol in mL) as compared to the weight of compound of Formula I (in g).

In an embodiment of the present invention, the amount of organic base used may range from 3-6 equivalents (in moles) and amount of phase transfer catalyst ranges from 1-1.5 equivalents (in moles) as compared to the amount in moles of compound of Formula I.

The reaction is performed by stirring of the reaction mass at a temperature of 30-35° C., for the time duration of 5-20 mins.

Step b) comprises heating the reaction mixture at 70-80° C.;

The reaction mass obtained in step a) is heated to a temperature ranging between 70-80° C. and stirring was performed for time duration ranging between 20-30 hrs at the same raised temperature.

Step c) comprises adding water to the reaction mass obtained in step b);

On completion of the reaction as confirmed by TLC (Thin Layer Chromatography), 3-35 times water (in mL) w.r.t. weight of compound of Formula I (in g) is added to the reaction mixture. The reaction mass is further stirred for time duration ranging from 30-60 minutes. Frequent reaction monitoring may be performed so as to avoid unnecessary delay in the further progress of the reaction.

Step d) comprises cooling the reaction mixture to a temperature below 35° C.;

The reaction mass obtained in step c) is slowly cooled to a temperature below 35° C., preferably ~30° C., at a rate of not exceeding 1° C./min. At this lowered temperature reaction mass is stirred for time duration ranging between 1-3 hrs depending upon the progress of the reaction.

Step e) comprises filtering and drying the material obtained in step d);

The reaction mass obtained in step d) is filtered by any conventional method such as micron filter paper to obtain a solid material. This solid material may be given washing with water or an acetonitrile-water (1:1) mixture. Then this solid material is dried by using conventional drying methods like suck drying, air drying, drying under reduced pressure conditions and/or drying at increased temperature. Reduced pressure conditions for e.g. vacuum, if required for drying may be suitably employed by the person having skill in the art. Drying process is carried out for time duration ranging between 8-12 hrs.

Step f) comprises optionally purifying the product obtained from step e);

The product obtained in step e) is generally obtained with HPLC purity of greater than 99.5%. But if the end product does not meet the purity standard of HPLC purity greater than 99.5%, then optionally further purification steps may be performed.

Purification of the product obtained from step e) may be performed by providing a solution of this low purity product in $C_{1-4}$ alcohol and water at a temperature of 30-35° C. $C_{1-4}$ alcohol may be selected from methanol, ethanol, n-propanol or iso-propanol. The amount of $C_{1-4}$ alcohol and water used in this reaction ranges from 15-30 times (vol. in mL) and 2-5 times (vol. in mL) resp. w.r.t. the amount of product obtained from step e). In one particular embodiment for 12.0 g product obtained from step e), 264 mL ethanol and 36 mL water was used. The reaction mass is stirred for time duration of 5-20 mins.

Then the reaction mass temperature is raised to a temperature ranging between 75-80° C., wherein stirring may be performed for time duration ranging between 1-3 hrs. Optionally in between the stirring, the reaction mass may be filtered through celite bed and again washed with $C_{1-4}$ alcohol and water. Further, 6-10 times (vol. in mL) water w.r.t. the amount of product obtained from step e) is added to the reaction mass during the stirring process. After completion of stirring the reaction mixture is slowly cooled to a temperature of 30-35° C.

The reaction mass is then filtered to obtain a solid material which is given washing with $C_{1-4}$ alcohol-water (1:1) mixture. Then this solid material is dried for time duration of 8-12 hrs by using conventional drying methods like suck drying, air drying, drying under reduced pressure conditions and drying at increased temperature of 50-55° C.

Step g) comprises isolating crystalline Dasatinib monohydrate.

The dried reaction mass obtained from step e) or f) is cooled to a temperature below 35° C. and brought to normal room environment to obtain off white to pale yellow coloured pure crystals of Dasatinib monohydrate.

Process of isolating crystalline Dasatinib monohydrate may further comprise processes but not limited to conventional processes including scrapping, if required filtering from slurry to retain the crystalline form characteristics.

The merit of the process according to the present invention resides in that—the process related impurities, including unreacted intermediates, side products, degradation products and other medium dependent impurities, that appear in the impurity profile of the Dasatinib monohydrate may be substantially removed by the process of the present invention resulting in the formation of substantially pure Dasatinib monohydrate. Substantially pure Dasatinib monohydrate obtained according to the process of the present invention results in the final API purity (by HPLC) of more than 99.5% w/w. The yield of the process of the present invention is significantly higher (>92%) than those of the prior art reported processes.

Figure 2:
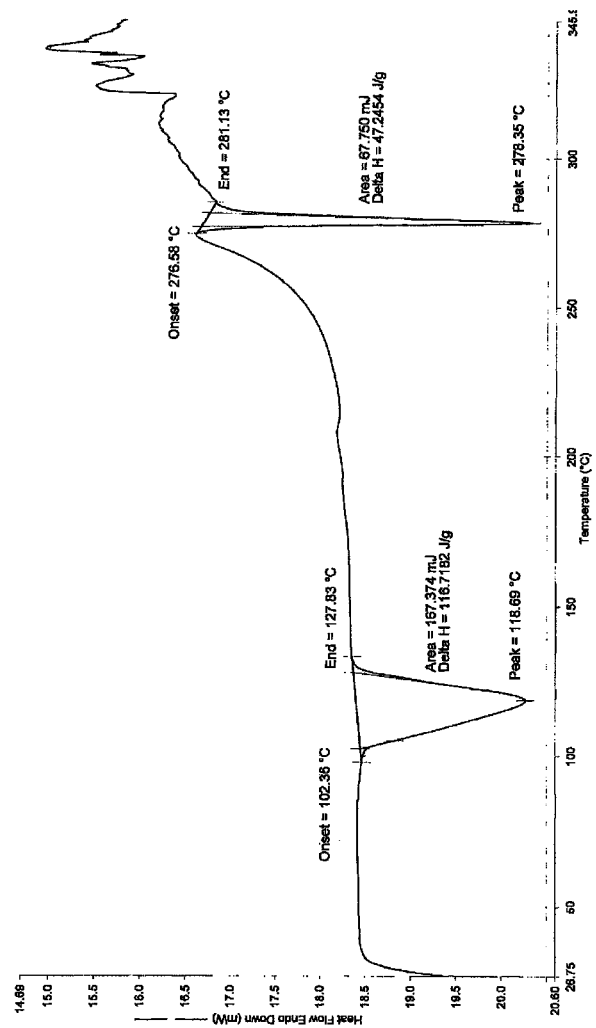
FIG. 2 is DSC of Dasatinib monohydrate obtained according to the process of example 1.

In one embodiment of the present application the reaction mentioned is carried out without isolating the Dasatinib free base, though sometimes the free base form of Dasatinib may also be isolated before proceeding for the preparation of Dasatinib monohydrate. Process for preparing Dasatinib monohydrate according to the present invention provides crystalline Dasatinib monohydrate characterized by X-ray powder diffraction pattern as per FIG. 1 and DSC pattern as per FIG. 2. The moisture content of the end product obtained is between 3.4 to 4.2%.

The crystalline Dasatinib monohydrate described herein may be characterized by X-ray powder diffraction pattern (XRPD) and thermal techniques such as differential scanning calorimetry (DSC) analysis. The samples of Dasatinib monohydrate obtained by the process of the present invention were analyzed by XRPD on a Bruker AXS D8 Advance Diffractometer using X-ray source—Cu Kα radiation using the wavelength 1.5418 Å and lynx Eye detector. DSC was done on a Perkin Elmer Pyris 7.0 instrument. Illustrative examples of analytical data for the crystalline Dasatinib monohydrate obtained in the examples are set forth in the FIGS. 1-2.

Another embodiment of the present invention provides a method for the preparation of 2-((6-chloro-2-methylpyrimidin-4-yl)amino)-N-(2-chloro-6-methylphenyl)thiazole-5-carboxamide i.e. compound of Formula I,

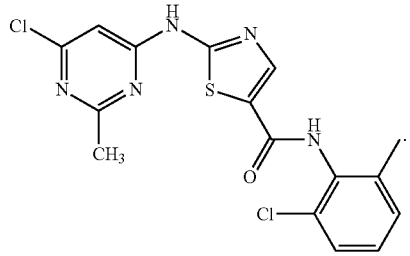

which is used as a key starting material in the process of preparation of Dasatinib monohydrate according the present invention. Though the compound of Formula I to be used for preparation of Dasatinib monohydrate according to process of current application, can be prepared by any of the method described in prior art, but the present process provides the advantage of higher yield and hence is more economical.

In a further embodiment of the present application, compound of Formula I is prepared by reaction of 2-amino-N-(2-chloro-6-methyl phenyl)-5-thiazole carboxamide with 4,6-dichloro-2-methyl pyrimidine in the presence of sodium amide (NaNH$_2$).

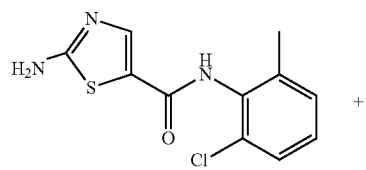

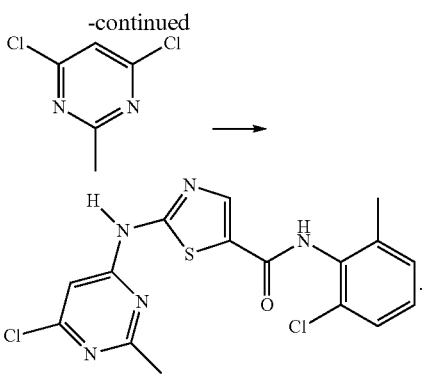

4,6-Dichloro-2-methyl pyrimidine and 2-amino-N-(2-chloro-6-methyl phenyl)-5-thiazole carboxamide are reacted in presence of sodium amide in an organic solvent like THF. The reaction may be performed under inert conditions like N$_2$ atmosphere. The amount of sodium amide used in the reaction may range from 3-6 equivalents (by molar ratio) w.r.t. amount of 2-amino-N-(2-chloro-6-methyl phenyl)-5-thiazole carboxamide.

The reaction mass obtained above is added to another lot of THF at 5-10° C., wherein an exothermic reaction takes place. Stirring of the reaction mass is performed for time duration of 3-6 hrs initially at low temperature and then at ~RT.

On completion of the reaction as confirmed by TLC, the reaction mass is again cooled to a temperature ~0° C. and pH adjusted to 3-4 using suitable acidic reagents. After stirring for 2-4 hrs the reaction mass is filtered, dried and added to DMF solution. The reaction mass is then heated to temperature ranging between 60-70° C., maintained for 30-60 mins, slowly cooled to 30-35° C., filtered and dried to obtain 2-((6-chloro-2-methylpyrimidin-4-yl) amino)-N-(2-chloro-6-methylphenyl)thiazole-5-carboxamide i.e. compound of Formula I.

Certain specific aspects and embodiments of the present application will be explained in more detail with reference to the following examples, which are provided by way of illustration only and should not be construed as limiting the scope of the invention in any manner.

EXAMPLES

Reference Example-01

Process for preparation of 2-((6-chloro-2-methylpyrimidin-4-yl) amino)-N-(2-chloro-6-methylphenyl) thiazole-5-carboxamide (I)

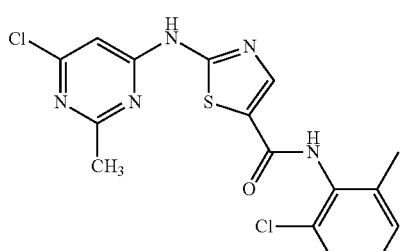

Into a RBF 6.6 g of Sodium Amide was added at 30-35° C. under $N_2$ atmosphere and stirring was done for 10-15 minutes. Then the reaction mass was cooled to 5-10° C. and 120.0 mL THF and 7.92 g 4,6-Dichloro-2-methyl pyrimidine were added to the reaction mass. Addition of 10.0 g 2-amino-N-(2-chloro-6-methyl phenyl)-5-thiazole carboxamide was then performed into the reaction mass. The reaction mass was stirred for ~40 mins at 30-35° C. to get clear solution which was transferred to an addition dropper. At temperature of 5-10° C., the reaction mass was slowly added over 30 minutes, into another RBF having 40.0 mL THF. At the same temperature, the reaction mass was stirred for 1.0-1.5 hrs. Then the reaction mass temperature was increased to 30-35° C., where stirring was performed for 3 to 4 hrs. On completion of the reaction as verified by TLC, the reaction mass was cooled slowly to a temperature of 0-5° C. Then the reaction mass pH was adjusted to 3-4 by addition of 22.4 mL HCl and 240 mL water over 10-15 mins. The reaction mass was then stirred for 2.0-2.5 hrs at 0-5° C.

After the completion of stirring the reaction mass was filtered and washed with 20 mL water. The compound was then suck dried at RT for 10-15 mins. The wet compound was then unloaded and added to a RBF containing 12.0 mL DMF. The reaction mass was then heated to 65-70° C. for ~45 mins. Then the reaction mass was slowly cooled to a temperature of 30-35° C. and stirring was performed for ~45 mins. The reaction mass was then filtered and washed with 1 mL DMF. The material obtained was suck dried for 10-15 mins at RT, unloaded and air dried for 30 mins. Then the material was further dried under vacuum: for 1 h at 30-35° C., followed by ~8 h drying at temperature of ~65° C. After this, the solid material was cooled to 30-35° C. and the vacuum was released to obtain the dry 2-((6-chloro-2-methylpyrimidin-4-yl)amino)-N-(2-chloro-6-methylphenyl)thiazole-5-carboxamide material. (HPLC Purity ~97.0%, Yield: ~60%)

Example 1

Preparation of Dasatinib Monohydrate

Take 12 ml of acetonitrile in RB flask and charge 1 g of 2-((6-chloro-2-methylpyrimidin-4-yl)amino)-N-(2-chloro-6-methylphenyl)thiazole-5-carboxamide (Formula I), 1.98 g of 1-(2-Hydroxyethyl)piperazine (Formula II), 1.28 g of triethyl amine and 1.02 g of TBAB. Stir the reaction mass for 10-15 min at 30-35° C. Heat the reaction mixture to 75-80° C. and stir for 20-24 h. Check for the completion of reaction with Thin Layer Chromatography (TLC). Charge 4 mL of water slowly and stir the reaction mass for 30-45 mins at 75° C. Cool the reaction mass to 30-35° C. and stir for 2-3 hrs. Filter the reaction mass and wash with acetonitrile and water mixture (1:1). Dry the material to get 1.15 g of crystalline Dasatinib monohydrate.

Yield—93% HPLC Purity—99.7%

Example 2

Preparation of Dasatinib Monohydrate 200 ml of acetonitrile was taken in RB flask and 10.0 g of 2-((6-chloro-2-methylpyrimidin-4-yl)amino)-N-(2-chloro-6-methylphenyl)thiazole-5-carboxamide (Formula I), 19.8 g of 1-(2-Hydroxyethyl)piperazine (Formula II), 12.85 g of triethyl amine and 10.0 g of TBAB were charged into it. The reaction mass was stirred for 10-15 mins at 30-35° C. and then heated to 80° C. and stirred for 20-22 h. The completion of reaction was checked with Thin Layer Chromatography (TLC) and 300 mL of water was slowly charged. The reaction mass was stirred for 45 mins at 80° C. and then cooled to 30-35° C. and further stirred for ~1.5 hrs. The reaction mass was filtered, washed with 20 mL water and suck dried for 10-15 min at RT. The wet compound was unloaded and air dried for 30 mins at 30-35° C. The material was loaded to a vacuum tray drier at 30-35° C. and vacuum was applied. The material was dried at 30-35° C. for 1 h and slowly dryer temperature was raised to 50-55° C. where drying was carried out for 8-10 hrs. The solid product obtained was then cooled to 30-35° C. and vacuum was released to obtain 12.5 g of the title compound.

Yield—97% HPLC Purity—99.42%

Example 3

Preparation of Dasatinib Monohydrate with Purity Greater than 99.5% from a Sample with Lesser Purity 264.0 mL ethanol and 36 mL water was charged in to RBF at 30-35° C. and 12.0 g Dasatinib Monohydrate as obtained in Example-2 was added to it. The reaction mass was stirred for 10-15 mins and the reaction temperature was raised to 75-80° C., where further stirring was performed for 20-30 mins. 5.0 g celite was added to the reaction mass and it was filtered through celite bed. The celite bed was washed with mixture of 21.0 mL ethanol and 2.8 mL water. The reaction mass temperature was raised to 75-80° C. and 96.0 mL water was added, followed by stirring for ~50 mins. Then the reaction mass temperature was slowly cooled to 30-35° C., after which filtration was performed. The reaction mass was washed with mixture of 12.0 mL ethanol and 12.0 mL water. The obtained reaction mass was suck dried for 10-15 mins, unloaded, air dried for 30 mins and then loaded into a vacuum tray drier and vacuum was applied. The material was dried at 30-35° C. for 1 h and slowly dryer temperature was raised to 50-55° C. where drying was carried out for 8-12 hrs. Then product was cooled to 30-35° C. and vacuum was released to obtain 11.1 g of title compound as an off white to pale yellow colored crystalline solid.

Yield: 92% HPLC Purity: 99.74% Moisture content: 3.73%

While the foregoing provides a detailed description of the preferred embodiments of the invention, it is to be understood that the descriptions are illustrative only of the principles of the invention and not limiting. Furthermore, as many changes can be made to the invention without departing from the scope of the invention, it is intended that all material contained herein be interpreted as illustrative of the invention and not in a limiting sense.

We claim:

1. A process for the preparation of Dasatinib monohydrate of Formula A,

Formula A

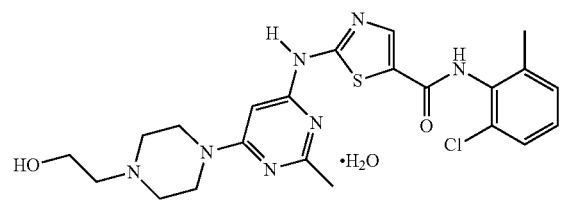

comprising the steps of:
a) reacting the compound of Formula I with 1-(2-Hydroxyethyl)piperazine (Formula II) in the presence of acetonitrile solvent, an organic base and a phase transfer catalyst;

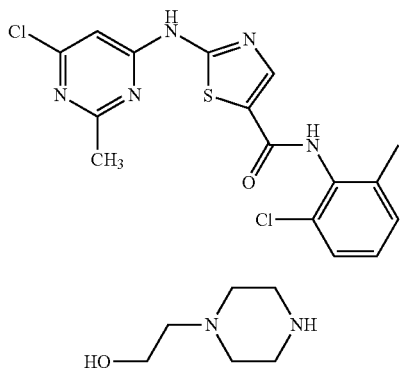

b) heating the reaction mixture at 50-80° C.;
c) adding water to the reaction mass obtained in step b);
d) cooling the reaction mixture to a temperature below 35° C.;
e) filtering and drying the material obtained in step d);
f) optionally purifying the product obtained from step e);
g) isolating crystalline Dasatinib monohydrate.

2. The process for the preparation of Dasatinib monohydrate according to claim 1, wherein compound of Formula I is prepared by reaction of 2-amino-N-(2-chloro-6-methyl phenyl)-5-thiazole carboxamide with 4,6-dichloro-2-methyl pyrimidine in the presence of sodium amide ($NaNH_2$).

3. The process for the preparation of Dasatinib monohydrate according to claim 1, wherein the organic base is selected from triethyl amine (TEA), diisopropylethyl amine (DIPEA), t-butylamine or propyl amine.

4. The process for the preparation of Dasatinib monohydrate according to claim 1, wherein the phase transfer catalyst is selected from tetrabutyl ammonium bromide (TBAB), tetrabutyl ammonium fluoride (TBAF) or benzyl triethyl ammonium chloride.

5. The process for the preparation of Dasatinib monohydrate according to claim 1, wherein optional step f) comprises the steps of:
 a) providing a solution of product obtained from step e) of claim 1 in $C_{1-4}$ alcohol and water;
 b) raising the reaction temperature to 75-80° C.;
 c) subjecting the reaction mass to continuous stirring;
 d) slowly cooling the reaction mixture to a temperature of 30-35° C.;
 e) filtering and drying the material obtained.

6. The process for the preparation of Dasatinib monohydrate according to claim 5, wherein $C_{1-4}$ alcohol is selected from methanol, ethanol, n-propanol or iso-propanol.

7. The process for the preparation of Dasatinib monohydrate according to claim 1, wherein the process of isolation of pure crystals of Dasatinib monohydrate includes cooling of the reaction mass to a temperature below 35° C.

8. The process for the preparation of Dasatinib monohydrate according to claim 1, wherein the moisture content of the end product obtained in step g) is between 3.4 to 4.2%.

9. A process for the preparation of Dasatinib monohydrate of Formula A,

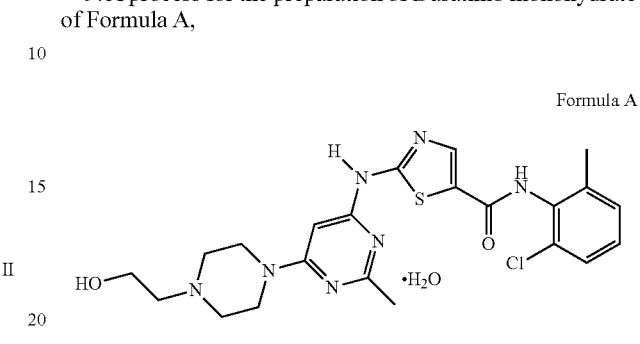

comprising
a) reacting the compound of Formula I with 1-(2-Hydroxyethyl)piperazine (Formula II) in the presence of acetonitrile solvent, an organic base and a phase transfer catalyst at a temperature ranging between 50-80° C., followed by adding water;

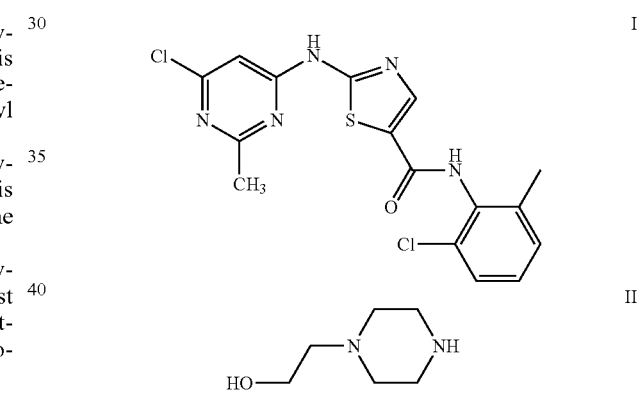

b) isolating the crystalline Dasatinib monohydrate.

10. The process for the preparation of Dasatinib monohydrate according to claim 9, wherein the organic base is selected from triethyl amine (TEA), diisopropylethyl amine (DIPEA), t-butylamine or propyl amine.

11. The process for the preparation of Dasatinib monohydrate according to claim 9, wherein the phase transfer catalyst is selected from tetrabutyl ammonium bromide (TBAB), tetrabutyl ammonium fluoride (TBAF) or benzyl triethyl ammonium chloride.

* * * * *